(12) United States Patent
Robertson et al.

(10) Patent No.: US 8,286,498 B1
(45) Date of Patent: Oct. 16, 2012

(54) METHOD AND DEVICE FOR TENSILE TESTING OF CABLE BUNDLES

(75) Inventors: Lawrence M. Robertson, Albuquerque, NM (US); Emil V. Ardelean, Albuquerque, NM (US); James C. Goodding, Albuquerque, NM (US); Vit Babuska, Albuquerque, NM (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 283 days.

(21) Appl. No.: 12/852,562

(22) Filed: Aug. 9, 2010

(51) Int. Cl.
*G01N 3/08* (2006.01)
(52) U.S. Cl. .......................................................... 73/826
(58) Field of Classification Search ...................... 73/826
See application file for complete search history.

(56) References Cited

U.S. PATENT DOCUMENTS

| | | | | |
|---|---|---|---|---|
| 2,814,883 A * | 12/1957 | Strimel | ........................... | 33/789 |
| 3,129,583 A * | 4/1964 | Cosner | ........................... | 73/789 |
| 3,138,952 A * | 6/1964 | Dobbins | ........................ | 73/793 |
| 3,425,131 A * | 2/1969 | Hooper | .......................... | 33/790 |
| 3,696,512 A * | 10/1972 | Von Marinelli et al. | ........ | 33/790 |
| 4,535,636 A * | 8/1985 | Blackburn et al. | .............. | 73/831 |
| 4,848,161 A * | 7/1989 | van der Kuur | .................. | 73/760 |
| 5,083,465 A * | 1/1992 | Myers | .............................. | 73/826 |
| 5,361,640 A * | 11/1994 | Carroll et al. | ................... | 73/831 |
| 8,210,050 B2 * | 7/2012 | Myers | .............................. | 73/808 |

FOREIGN PATENT DOCUMENTS

JP    09-033416    *  7/1997

* cited by examiner

*Primary Examiner* — Lisa Caputo
*Assistant Examiner* — Octavia Davis-Hollington
(74) *Attorney, Agent, or Firm* — James M. Skorich; Kenneth E. Callahan

(57) ABSTRACT

A standard tensile test device is improved to accurately measure the mechanical properties of stranded cables, ropes, and other composite structures wherein a witness is attached to the top and bottom mounting blocks holding the cable under test. The witness is comprised of two parts: a top and a bottom rod of similar diameter with the bottom rod having a smaller diameter stem on its upper end and the top rod having a hollow opening in its lower end into which the stem fits forming a witness joint. A small gap is present between the top rod and the larger diameter portion of the bottom rod. A standard extensometer is attached to the top and bottom rods of the witness spanning this small witness gap. When a force is applied to separate the mounting blocks, the gap in the witness expands the same length that the entire test specimen is stretched.

3 Claims, 3 Drawing Sheets

Schematic of Standard Tensile Test Device

Elongation/Strain Measurement Details

METHOD AND DEVICE FOR TENSILE TESTING OF CABLE BUNDLES

STATEMENT OF GOVERNMENT INTEREST

This invention was developed under Contract DE-AC04-94AL85000 between Sandia Corporation and the U.S. Department of Energy. The U.S. Government has certain rights in this invention.

BACKGROUND OF THE INVENTION

The invention relates generally to devices used for tensile testing of cables, and in particular to a tensile testing device for use with electrical cables and other non-standard composite cables in which elongation data of the entire sample is measured.

Mechanical properties of electrical power and signal cables found on precision spacecraft or other systems must be known if accurate structural models of cabled structures are desired. Until recently electrical cables were not considered an important contributor to the overall dynamics of cabled structures. However, the mass of cables relative to the overall structure mass has increased significantly over the last couple of decades as the complexity of structures increased. This trend motivated attempts to develop modeling tools able to accurately capture the dynamics of cabled structures. Cables are composite structures of individual wires twisted together with large fabrication variability and consequently development of analytical models based on properties of individual components is not a feasible approach. The experimental determination of the mechanical properties of cables through tensile (axial) and lateral tests is much more effective.

The standard tensile test device uses an extensometer mounted directly on the specimen as seen in FIG. 1. The ends of the specimen are pulled apart by the testing frame and load F is measured with a load cell. The extensometer is mounted directly on the specimen under test and measures the specimen's elongation between its two knife edges. The resulting stress measurement can then be reasonably extrapolated for the entire specimen's length for isotropic structures. Testing of composite electrical cables in this manner is not possible mainly because the extensometer cannot be placed directly on the sample. Placing the extensometer directly on the sample leads to erroneous data as the cable surface is not uniform and knife edges can slip. Additionally, cables are not isotropic structures and tend to twist during testing due to their construction. Therefore, strain measurements on a short cable length may not be accurate for the whole cable length. However, if strain is calculated based on the elongation of the entire sample, which must be long enough to be representative, a more reliable value is obtained. One way to measure elongation of the entire sample is by recording the displacement of the testing frame's cross-head displacement, but this leads to erroneous results because of the compliance associated with the fixtures (grips, connecting elements, etc). The present invention is designed to overcome these limitations.

SUMMARY

The present invention adapts a standard tensile test device to accurately measure the mechanical properties of stranded cables, ropes, and other composite structures. A standard tensile test device has a test specimen mounted between upper and lower blocks. An extensometer is mounted on a small portion of the test specimen and measures the elongation or strain of that portion of the test specimen under a force or stress applied to separate the upper and lower mounting blocks. The mechanical properties of composite structures such as stranded cables cannot be accurately measured using these prior art devices. Only the strain of a small portion of the cable is measured and this cannot be extrapolated to the entire length of the test specimen.

The present invention employs a standard tensile test device but with the standard extensometer mounted on a witness rather than directly on the specimen. The witness is comprised of two parts: a top and a bottom rod of similar diameter with the bottom rod having a smaller diameter stem on its upper end and the top rod having a hollow opening in its lower end into which the stem fits forming a witness joint. The witness is attached to the same mounting blocks as the test specimen with a small gap present between the top rod and the larger diameter portion of the bottom rod. A standard extensometer is attached to the top and bottom rods of the witness spanning this small witness gap. When a force is applied to separate the mounting blocks, the gap in the witness expands the same length that the entire test specimen is stretched. The elongation of the entire length of the test specimen is thereby measured using a standard extensometer and yielding a more accurate strain measurement.

DESCRIPTION OF THE PREFERRED EMBODIMENT

Figure 1:
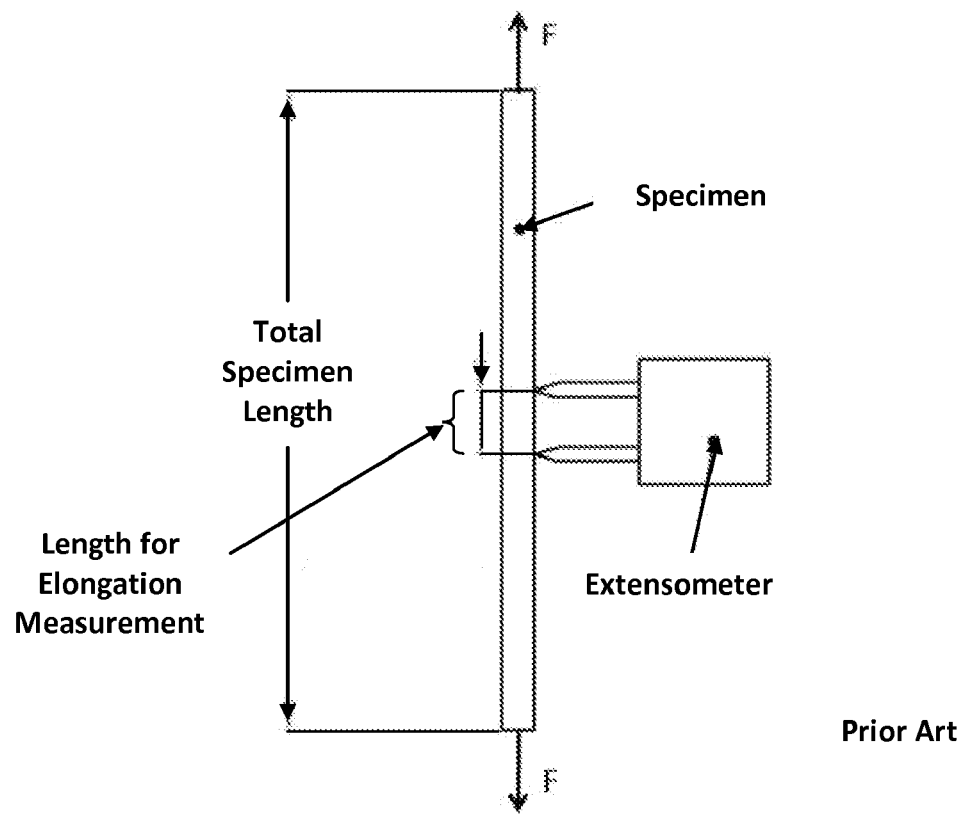
FIG. 1 is a schematic of a standard tensile test known is the prior art.
Figure 2:
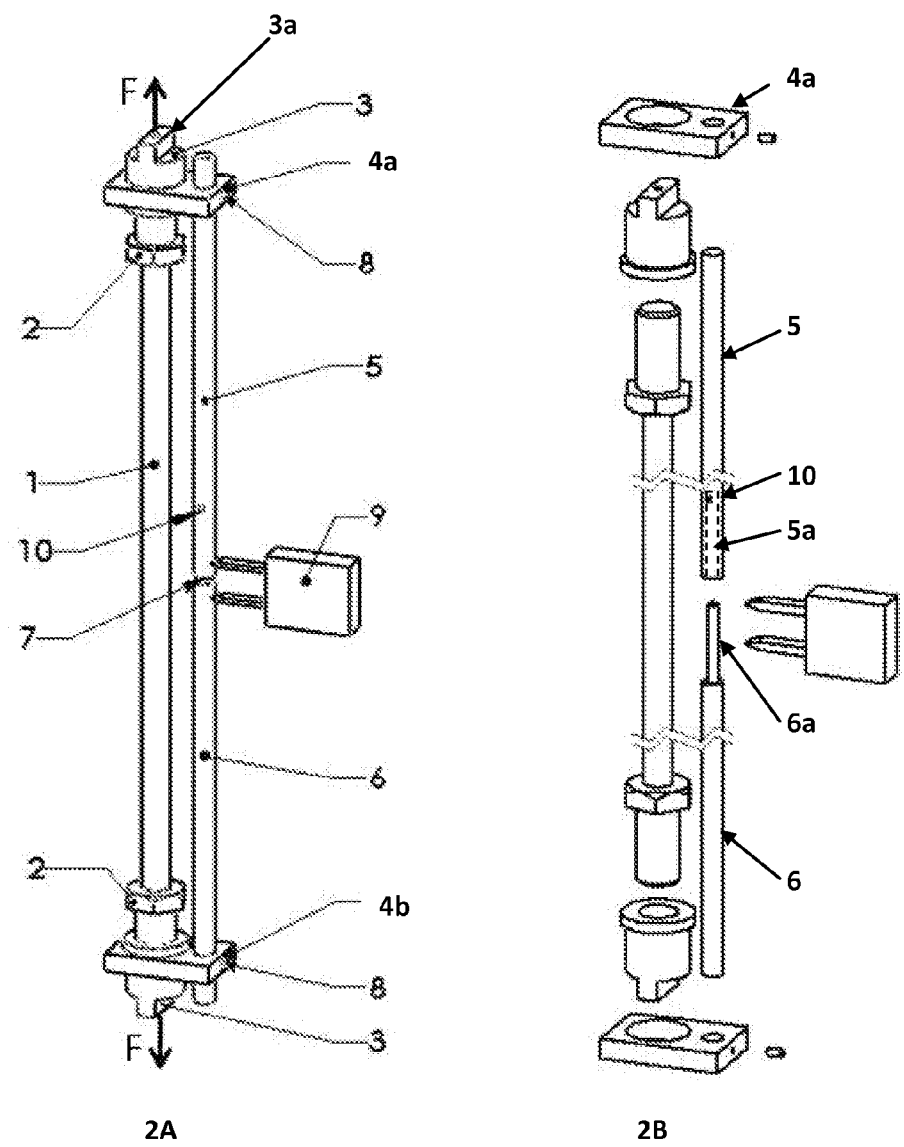
FIG. 2 shows a schematic of the tensile test device of the present invention in a working configuration (2A) and in an exploded view (2B).

FIG. 2A is a schematic of the device in its working configuration and FIG. 2B is an exploded view of the device. The specimen under test 1 is firmly attached at each end by cable holders 2. The means for attaching the cable specimen to the cable holders may be glue or a mechanical means. The specimen cable must fit snuggly in the cable holder holes to assure proper alignment during testing. The cable holders 2 are securely mounted in grip adapters 3. The flat tabs 3a at the far end of each grip adapter 3 fit in the mounting blocks 4 and provide alignment as well. Load F is applied by the top 4a and bottom 4b mounting blocks pulling apart the grip adapters 3. The grip adapters 3 and the cable holders 2 must be sufficiently stiff so their compliance is negligible compared with that of the cable specimen.

Figure 3:
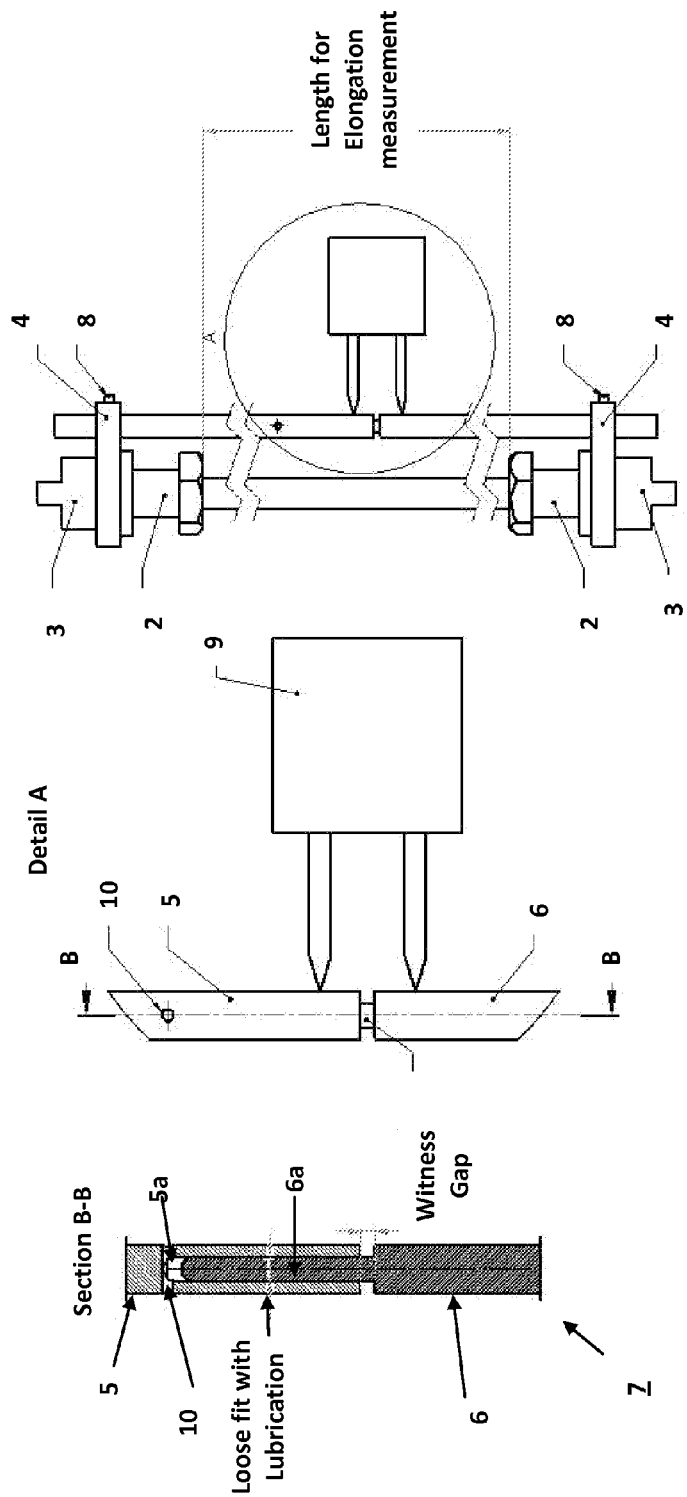
FIG. 3 shows details of the elongation/strain measurement device.

In the present invention, cable elongation is indirectly measured by using a witness comprised of a top rod 5 and a bottom rod 6, of the same diameter and a witness joint 7. The upper portion of the bottom rod 6 has a smaller diameter defining a stem 6a that is designed to fit into a hole 5a of slightly larger diameter than the stem in the bottom portion of the top rod 5. This stem-hole structure 6a, 5a comprising the witness joint 7 must be longer than the anticipated stretch of the cable under test and be lubricated so as to introduce negligible load during testing. In addition, in order to avoid an air spring in the witness joint 7 the top rod 5 has a relief hole 10 at the upper end of the top rod hole 5a. The bottom rod stem 6a and top rod hole 5a of the witness is shown in FIG. 2B as being entirely detached. As seen in FIG. 3 the stem 6a of the bottom rod 6 fits into the hole 5a machined into the top rod 5 in its operating configuration with a small gap.

The ends of the top 5 and bottom rods 6 opposite the witness joint ends are attached to the top 4a and bottom 4b mounting blocks, respectively, and provide proper alignment of the witness with the specimen. Set screws 8 may be used to fix the witness ends to the mounting blocks 4 once the cable specimen is ready for measurements and a small witness gap at the witness joint 7 (see FIG. 3A) is set. A standard extensometer 9 is placed across the witness gap between the top and bottom witness rods (see FIG. 3B). As a load is applied through the testing frame crosshead (not shown), the top rod 5 moves with the cable's top end and the extensometer 9 records the elongation of the entire cable specimen (see FIG. 3C). One can easily calculate strain by dividing the cable's elongation to its length. Extensional modulus can then be calculated from the strain-stress data. In addition the ultimate strength and elongation can be determined if desired.

The device can be used to measure the mechanical properties of stranded cables, ropes, and other composite structures.

The invention claimed is:

1. A method for testing mechanical properties of composite cable specimens, said specimen having a top end, a bottom end, and an at rest length, the method comprising:
    a. securely fastening the top end of a cable specimen to a top mounting block and the bottom end of said specimen to a bottom mounting block;
    b. securely fastening a witness to said top and bottom mounting blocks, said witness comprised of a top rod securely attached to said top mounting block at one rod end and having a hollow opposite rod end and a bottom rod securely attached to said bottom mounting block at one rod end and having a stem opposite rod end, said stem fitting within said hollow end of said top rod such that said top and bottom rods of said witness can freely move together or apart directly with any corresponding movement of said top and bottom mounting blocks;
    c. applying a force to separate said top and bottom mounting blocks; and
    d. measuring any displacement between said top and bottom witness rods resulting from the application of said separating force, whereby said measured displacement of the witness is a measurement of the increased length of the entire cable specimen from its at rest length and from which measurement mechanical properties of said specimen may be determined.

2. An improvement to a standard tensile test device having a top mounting block and a bottom mounting block to which a top end of a cable specimen of a known at rest length is securely attached to the top mounting block and a bottom end of said cable specimen is securely attached to the bottom end of the bottom mounting block and an extensometer to measure a portion of any length elongation of said cable specimen caused by a force applied to separate said top and bottom mounting blocks, said improvement comprising:
    a. a witness securely fastened to said top and bottom mounting blocks, said witness comprised of a top rod securely attached to said top mounting block at one rod end and having a hollow opposite rod end and a bottom rod securely attached to said bottom mounting block at one rod end and having a stem opposite rod end, said stem fitting within said hollow end of said top rod such that said top and bottom rods of said witness can freely move together or apart directly with any corresponding movement of said top and bottom mounting blocks; and
    b. an extensometer to measure any separation between said top and bottom witness rods caused by the application of a separating force between said top and bottom mounting blocks, whereby said measured displacement of the witness is a measurement of the increased length of the entire cable specimen from its at rest length and from which measurement mechanical properties of said cable specimen may be determined.

3. The improved standard tensile test device of claim 2, wherein there is a relief hole at the top of the hollow portion of the top witness rod.

* * * * *